(12) United States Patent
Thierbach et al.

(10) Patent No.: US 6,667,166 B2
(45) Date of Patent: Dec. 23, 2003

(54) PROCESSES FOR PREPARING D-PANTOTHENIC ACID USING CORYNEFORM BACTERIA

(75) Inventors: Georg Thierbach, Bielefeld (DE); Nicole Dusch, Werther (DE)

(73) Assignee: Degussa AG, Duesseldorf (DE)

( * ) Notice: Subject to any disclaimer, the term of this patent is extended or adjusted under 35 U.S.C. 154(b) by 108 days.

(21) Appl. No.: 09/887,054

(22) Filed: Jun. 25, 2001

(65) Prior Publication Data

US 2002/0068335 A1 Jun. 6, 2002

(30) Foreign Application Priority Data

Jun. 23, 2000 (DE) .......................................... 100 30 702

(51) Int. Cl.[7] ................................................ C12P 13/04
(52) U.S. Cl. ........................ 435/106; 435/183; 435/194; 435/252.3; 435/320.1
(58) Field of Search .................................. 435/106, 183, 435/194, 252.3, 320.1

(56) References Cited

FOREIGN PATENT DOCUMENTS

| EP | 1 006 189 | 6/2000 |
|----|-----------|--------|
| EP | 1 006 192 | 6/2000 |
| EP | 1 106 622 | 6/2001 |

OTHER PUBLICATIONS

Derwent Abstract, WO 00/77172, Dec. 21, 2000.

*Primary Examiner*—Ponnathapu Achutamurthy
*Assistant Examiner*—Christian L. Fronde
(74) *Attorney, Agent, or Firm*—Oblon, Spivak, McClelland, Maier & Neustadt, P.C.

(57) ABSTRACT

The present invention provides processes for preparing D-pantothenic acid using Coryneform bacteria having an enhanced pfkA gene.

16 Claims, 2 Drawing Sheets

PROCESSES FOR PREPARING D-PANTOTHENIC ACID USING CORYNEFORM BACTERIA

CROSS-REFERENCE TO RELATED APPLICATION

The present application claims priority to German Application No. DE10030702.7 filed Jun. 23, 2000, the entire contents of which are incorporated herein by reference

BACKGROUND OF THE INVENTION

1. Field of the Invention

The invention relates to a process for preparing D-pantothenic acid using Coryneform bacteria in which the pfkA gene is enhanced.

2. Discussion of the Background

Pantothenic acid is a vitamin of commercial importance which is used in cosmetics, medicine, human nutrition and animal nutrition.

Pantothenic acid can be prepared by chemical synthesis, or biotechnologically by fermentation of suitable microorganisms in suitable nutrient solutions. In chemical synthetic applications DL-pantolactone is an important intermediate stage. It is prepared in a multi-stage process from formaldehyde, isobutylaldehyde and cyanide. In further process steps, the racemic mixture is separated, D-pantolactone is subjected to a condensation reaction with β-alanine which yields the desired D-pantothenic acid.

The advantage of the fermentative preparation by microorganisms lies in the direct formation of the desired stereoisomeric D-form, which is free from L-pantothenic acid.

Various types of bacteria, such as, *Escherichia coli*, *Arthrobacter ureafaciens*, *Corynebacterium erythrogenes*, *Brevibacterium ammoniagenes*, and also yeasts, such as, *Debaromyces castellii*, can produce D-pantothenic acid in a nutrient solution which comprises glucose, DL-pantoic acid and β-alanine, as shown in EP-A 0 493 060. EP-A 0 493 060 further shows that in the case of *Escherichia coli*, the formation of D-pantothenic acid is improved by amplification of pantothenic acid biosynthesis genes from *E. coli* which are contained on the plasmids pFV3 and pFV5 in a nutrient solution comprising glucose, DL-pantoic acid and β-alanine.

EP-A 0 590 857 and U.S. Pat. No. 5,518,906 describe mutants derived from *Escherichia coli* strain IFO3547, such as FV5714, FV525, FV814, FV521, FV221, FV6051 and FV5069, which carry resistances to various antimetabolites, such as salicylic acid, α-ketobutyric acid, α-hydroxyaspartic acid, O-methylthreonine and α-ketoisovaleric acid. These strains produce pantoic acid in a nutrient solution comprising glucose, and produce D-pantothenic acid in a nutrient solution comprising glucose and β-alanine. EP-A 0 590 857 and U.S. Pat. No. 5,518,906 also show that after amplification of the pantothenic acid biosynthesis genes contained on the plasmid pFV31, in the abovementioned strains, the production of D-pantoic acid in nutrient solutions comprising glucose and the production of D-pantothenic acid in a nutrient solution comprising glucose and β-alanine is improved.

The knowledge with respect to processes for preparing D-pantothenic acid with the aid of *Corynebacterium glutamicum* are known only in some instances in the literature. Sahm and Eggeling (Applied and Environmental Microbiology 65(5), 1973–1979 (1999)) thus report on the influence of over-expression of the panB and panC genes and Dusch et al. (Applied and Environmental Microbiology 65(4), 1530–1539 (1999)) report on the influence of the panD gene on the formation of D-pantothenic acid.

However, there remains a need for improved methods of producing pantothenic acid in Coryneform bacteria. On a commercial or industrial scale even small improvements in the yield of pantothenic acid, or the efficiency of their production, are economically significant. Prior to the present invention, it was not recognized that enhancement of the pfkA gene in Coryneform bacteria would improve pantothenic acid.

SUMMARY OF THE INVENTION

One object of the present invention, is providing a new process for producing D-pantothenic acid by culturing a Coryneform bacteria comprising an enhanced pfkA gene and collecting the D-pantothenic acid produced. In preferred embodiments of the invention, the pfkA gene encodes a polypeptide comprising the amino acid sequence of SEQ ID NO:2 or which pfkA gene copmrprise SEQ ID NO:1. In another embodiment, the pfkA gene comprises those nucleotide sequences which hybridize under stringent conditions to SEQ ID NO:1 and encode a polypeptide having phosphofructokinase activity where the stringent conditions comprise washing in 5× SSC at a temperature of from 50 to 68° C.

Another object of the present invention is to prepare D-pantothenic acid having the enhance pfkA gene and also having enhanced expression of one or more of panB, panC, and/or ilvD.

In one embodiment the pfkA gene is enhanced by over-expression.

The above objects highlight certain aspects of the invention. Additional objects, aspects and embodiments of the invention are found in the following detailed description of the invention.

DETAILED DESCRIPTION OF THE INVENTION

Figure 1:
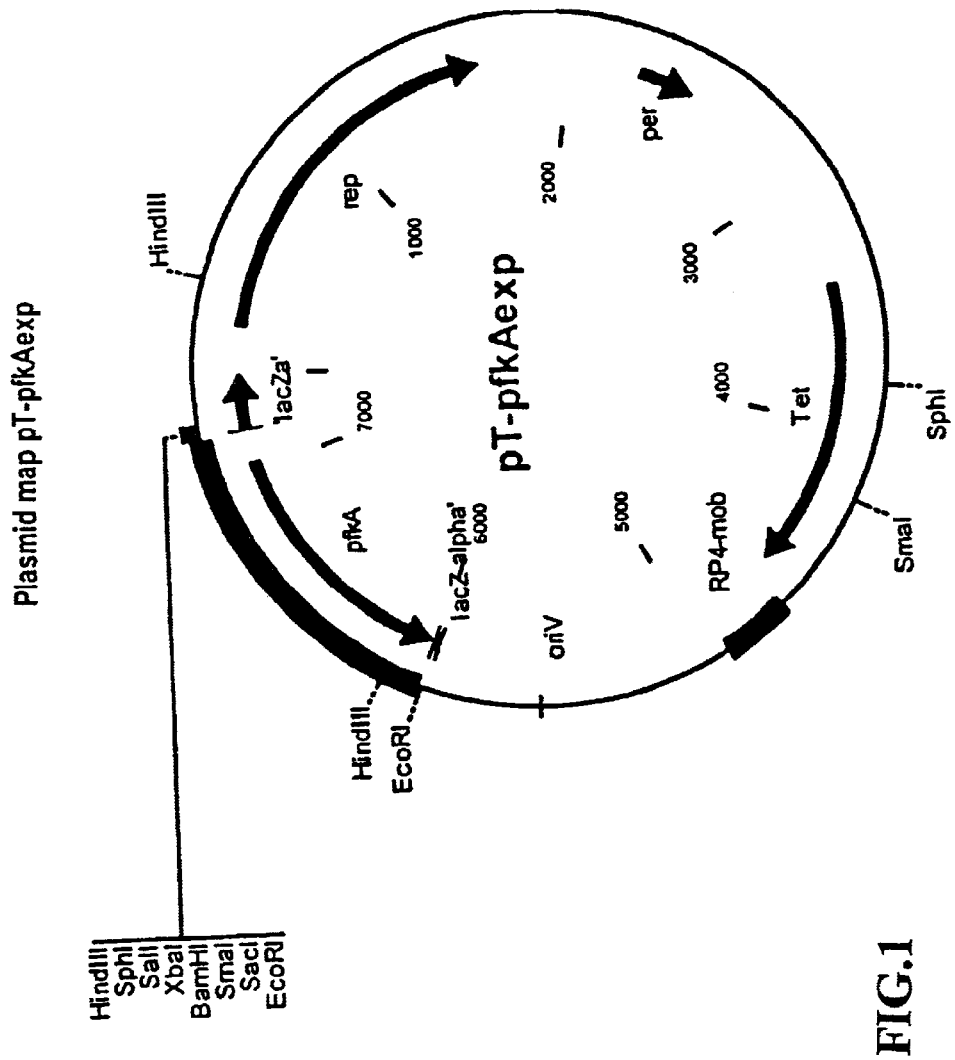
FIG. 1: Plasmid map of pT-pfkAexp

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In addition, the materials, methods, and examples are illustrative only and are not intended to be limiting.

Reference is made to standard textbooks of molecular biology that contain definitions and methods and means for carrying out basic techniques, encompassed by the present invention. See, for example, Maniatis et al., Molecular Cloning: A Laboratory Manual, Cold Spring Harbor Laboratory, New York (1982) and Sambrook et al., Molecular Cloning: A Laboratory Manual, Cold Spring Harbor Laboratory, New York (1989) and the various references cited therein.

The vitamin pantothenic acid is a product of commercial importance which is used in cosmetics, medicine, human nutrition and animal nutrition. There is a general interest in providing improved processes for the preparation of pantothenic acid.

As used herein "D-pantothenic acid", "pantothenic acid" or pantothenate include not only the free acids but also the salts of D-pantothenic acid, such as, the calcium, sodium, ammonium or potassium salts.

The invention provides a process for the fermentative preparation of D-pantothenic acid using coryneform bacteria in which the nucleotide sequence which codes for the enzyme phosphofructokinase (EC 2.7.1.11) (pfkA gene) is enhanced. Preferably, the pfkA gene is over-expressed.

The strains employed preferably already produce D-pantothenic acid before enhancement of the pfkA gene.

The term "enhancement" as used herein describes the increase in the intracellular activity of one or more enzymes in a microorganism which are coded by the corresponding DNA, for example by increasing the number of copies of the gene or genes, using a strong promoter or using a gene which codes for a corresponding enzyme having a high activity, and optionally combining these measures.

Preferably, a Coryneform bacteria with attenuated expression of a pfkA gene that encodes a polypeptide having phosphofructokinase will improve pantothenic acid productivity at least 1% compared to a bacteria which does not contain such an attenuated pfkA gene.

The microorganisms which the present invention provides can produce D-pantothenic acid from glucose, sucrose, lactose, fructose, maltose, molasses, starch, cellulose or from glycerol and ethanol. They are representatives of Coryneform bacteria, in particular of the genus Corynebacterium. Of the genus Corynebacterium, there may be mentioned in particular the species *Corynebacterium glutamicum*, which is known among experts for its ability to produce L-amino acids.

Suitable strains of the genus Corynebacterium, in particular of the species *Corynebacterium glutamicum*, are, for example, the known wild-type strains

*Corynebacterium glutamicum* ATCC13032

*Corynebacterium acetoglutamicum* ATCC15806

*Corynebacterium acetoacidophilum* ATCC13870

*Corynebacterium thermoaminogenes* FERM BP-1539

*Brevibacterium flavum* ATCC14067

*Brevibacterium lactofermentum* ATCC13869 and

*Brevibacterium divaricatum* ATCC14020 and D-pantothenic acid-producing mutants prepared therefrom, such as, for example

*Corynebacterium glutamicum* ATCC13032ΔilvA/ pEC7panBC

*Corynebacterium glutamicum* ATCC13032/pND-D2

It has been found that Coryneform bacteria produce pantothenic acid in an improved manner after overexpression of the pfkA gene, which codes for phosphofructokinase (EC 2.7.1.11).

The nucleotide sequence of the pfkA gene is shown in SEQ ID No 1 and the enzyme protein amino acid sequence resulting therefrom is shown in SEQ ID No 2.

The pfkA gene described in SEQ ID No 1 can be employed according to the invention. Alleles of the pfkA gene which result from the degeneracy of the genetic code or due to sense mutations of neutral function can furthermore be used. The polynucleotides of the invention include a polynucleotide according to SEQ ID No. 1 or a fragment prepared therefrom, and also polynucleotides that are at least especially from 70% to 80%, preferably at least from 81% to 85%, especially preferably at least from 86% to 90%, and very especially preferably at least 91%, 93%, 95%, 97% or 99%, identical with the polynucleotide according to SEQ ID No. 1, or with a fragment prepared therefrom.

Homology, sequence similarity or sequence identity of nucleotide or amino acid sequences may be determined conventionally by using known software or computer programs such as the BestFit or Gap pairwise comparison programs (GCG Wisconsin Package, Genetics Computer Group, 575 Science Drive, Madison, Wis. 53711). BestFit uses the local homology algorithm of Smith and Waterman, Advances in Applied Mathematics 2: 482–489 (1981), to find the best segment of identity or similarity between two sequences. Gap performs global alignments: all of one sequence with all of another similar sequence using the method of Needleman and Wunsch, J. Mol. Biol. 48:443–453 (1970). When using a sequence alignment program such as BestFit, to determine the degree of sequence homology, similarity or identity, the default setting may be used, or an appropriate scoring matrix may be selected to optimize identity, similarity or homology scores. Similarly, when using a program such as BestFit to determine sequence identity, similarity or homology between two different amino acid sequences, the default settings may be used, or an appropriate scoring matrix, such as blosum45 or blosum80, may be selected to optimize identity, similarity or homology scores.

Similarly polynucleotides which hybridize under stringent conditions to the pfkA gene described in SEQ ID No 1 and which have the activity of phosphofructokinase can be employed according to the invention.

The terms "stringent conditions" or "stringent hybridization conditions" includes reference to conditions under which a polynucleotide will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing).

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2× SSC (20× SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1× SSC at 55 to 60° C. Exemplary high stringency conditions include hybridization in 50% formamide, 1 M NaCl, 1% SDS at 37° C., and a wash in 0.1× SSC at 60 to 65° C.

Specificity is typically the function of post-hybridization washes, the critical factors being the ionic strength and temperature of the final wash solution. For DNA—DNA hybrids, the $T_m$ can be approximated from the equation of Meinkoth and Wahl, Anal. Biochem., 138:267–284 (1984): $T_m=81.5°$ C.+16.6 (log M)+0.41 (%GC)−0.61 (% form)−500/L; where M is the molarity of monovalent cations, %GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with approximately 90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, N.Y. (1993); and Current Protocols in Molecular Biology, Chapter 2, Ausubel, et al., Eds., Greene Publishing and Wiley-Interscience, New York (1995).

To achieve an enhancement (for example over-expression), for example the number of copies of the corresponding genes is increased, or the promoter and regulation region or the ribosome binding site upstream of the structural gene is mutated. Expression cassettes which are incorporated upstream of the structural gene act in the same way. By inducible promoters, it is additionally possible to increase the expression in the course of fermentative pantothenic acid formation. The expression is likewise improved by measures to prolong the life of the m-RNA. Furthermore, the enzyme activity is also increased by preventing the degradation of the enzyme protein. The genes or gene constructs are either present here in plasmids with a varying number of copies, or are integrated and amplified in the chromosome. Alternatively, an over-expression of the genes in question can furthermore be achieved by changing the composition of the media and the culture procedure.

Instructions in this context can be found by the skilled artisan, inter alia, in Martin et al. (Bio/Technology 5, 137–146 (1987)), in Guerrero et al. (Gene 138, 35–41 (1994)), Tsuchiya and Morinaga (Bio/Technology 6, 428–430 (1988)), in Eikmanns et al. (Gene 102, 93–98 (1991)), in European Patent Specification EPS 0 472 869, in U.S. Pat. No. 4,601,893, in Schwarzer and Pühler (Bio/Technology 9, 84–87 (1991), in Reinscheid et al. (Applied and Environmental Microbiology 60, 126–132 (1994)), in LaBarre et al. (Journal of Bacteriology 175, 1001–1007 (1993)), in Patent Application WO 96/15246, in Malumbres et al. (Gene 134, 15–24 (1993)), in Japanese Laid-Open Specification JP-A-10-229891, in Jensen and Hammer (Biotechnology and Bioengineering 58, 191–195 (1998)) and in known textbooks of genetics and molecular biology.

By way of example, the pfkA gene was over-expressed with the aid of plasmids.

Suitable plasmids are those which are replicated in coryneform bacteria. Numerous known plasmid vectors, such as, for example, pZ1 (Menkel et al., Applied and Environmental Microbiology (1989) 64: 549–554), pEKEx1 (Eikmanns et al., Gene 102:93–98 (1991)) or pHS2-1 (Sonnen et al., Gene 107:69–74 (1991)) are based on the cryptic plasmids pHM1519, pBL1 or PGA1. Other plasmid vectors, such as, for example, those based on pCG4 (U.S. Pat. No. 4,489,160), or pNG2 (Serwold-Davis et al., FEMS Microbiology Letters 66, 119–124 (1990)), or pAG1 (U.S. Pat. No. 5,158,891), can be used in the same manner.

Plasmid vectors which are moreover suitable are those with the aid of which the process of gene amplification by integration into the chromosome can be used, as has been described, for example, by Reinscheid et al. (Applied and Environmental Microbiology 60, 126–132 (1994)) for duplication or amplification of the hom-thrB operon. In this method, the complete gene is cloned in a plasmid vector which can replicate in a host (typically *E. coli*), but not in *C. glutamicum*. Possible vectors are, for example, pSUP301 (Simon et al., Bio/Technology 1, 784–791 (1983)), pK18mob or pK19mob (Schäfer et al., Gene 145, 69–73 (1994)), PGEM-T (Promega corporation, Madison, Wis., USA), pCR2.1-TOPO (Shuman (1994). Journal of Biological Chemistry 269:32678–84; U.S. Pat. No. 5,487,993), pCR®Blunt (Invitrogen, Groningen, Holland; Bernard et al., Journal of Molecular Biology, 234: 534–541 (1993)) or pEM1 (Schrumpf et al, 1991, Journal of Bacteriology 173:4510–4516). The plasmid vector which contains the gene to be amplified is then transferred into the desired strain of *C. glutamicum* by conjugation or transformation. The method of conjugation is described, for example, by Schäfer et al. (Applied and Environmental Microbiology 60, 756–759 (1994)). Methods for transformation are described, for example, by Thierbach et al. (Applied Microbiology and Biotechnology 29, 356–362 (1988)), Dunican and Shivnan (Bio/Technology 7, 1067–1070 (1989)) and Tauch et al. (FEMS Microbiological Letters 123, 343–347 (1994)). After homologous recombination by means of a "cross over" event, the resulting strain contains at least two copies of the gene in question.

By way of example, the process of gene amplification by integration into the chromosome was employed in the context of the present invention such as the plasmid vector pT-pfkAexp shown in FIG. 1.

For production of pantothenic acid, it may additionally be advantageous for one or more further genes which code for enzymes of the pantothenic acid biosynthesis pathway or the keto-isovaleric acid biosynthesis pathway, in addition to the gene which codes for phosphofructokinase, such as, for example, the panB gene which codes for ketopantoate hydroxymethyltransferase (Sahm et al., Applied and Environmental Microbiology, 65, 1973–1979 (1999)) or the panC gene which codes for pantothenate synthetase (Sahm et al., Applied and Environmental Microbiology, 65, 1973–1979 (1999)) or the ilvD gene which codes for dihydroxy-acid dehydratase to be enhanced, in particular over-expressed.

In addition to over-expression of phosphofructokinase, it may furthermore be advantageous for the production of pantothenic acid to eliminate undesirable side reactions (Nakayama: "Breeding of Amino Acid Producing Microorganisms", in: Overproduction of Microbial Products, Krumphanzl, Sikyta, Vanek (eds.), Academic Press, London, UK, 1982).

The microorganisms prepared according to the invention can be cultured continuously or discontinuously in the batch process (batch culture) or in the fed batch (feed process) or repeated fed batch process (repetitive feed process) for the purpose of pantothenic acid production. A summary of known culture methods are [sic] described in the textbook by Chmiel (Bioprozesstechnik 1. Einführung in die Bioverfahrenstechnik [Bioprocess Technology 1. Introduction to Bioprocess Technology (Gustav Fischer Verlag, Stuttgart, 1991)) or in the textbook by Storhas (Bioreaktoren und periphere Einrichtungen [Bioreactors and Peripheral Equipment] (Vieweg Verlag, Braunschweig/Wiesbaden, 1994)).

The culture medium to be used must meet the requirements of the particular microorganisms in a suitable manner. Descriptions of culture media for various microorganisms are contained in the handbook "Manual of Methods for General Bacteriology" of the American Society for Bacteriology (Washington D.C., USA, 1981). Sugars and carbohydrates, such as, for example, glucose, sucrose, lactose, fructose, maltose, molasses, starch and cellulose, oils and fats, such as, for example, soya oil, sunflower oil, groundnut oil and coconut fat, fatty acids, such as, for example, palmitic acid, stearic acid and linoleic acid, alcohols, such as, for example, glycerol and ethanol, and organic acids, such as, for example, acetic acid, can be used as the source of carbon. These substances can be used individually or as a mixture. Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture. Potassium dihydrogen phosphate or dipotassium hydrogen phosphate or the corresponding sodium-containing salts can be used as the source of phosphorus. The culture medium must furthermore comprise salts of metals, such as, for example, magnesium sulfate or iron sulfate, which are necessary for growth. Finally, essential growth substances, such as amino acids and vitamins, can be employed in addition to the abovementioned substances. Precursors of pantothenic acid, such as aspartate, β-alanine, ketoisovalerate, ketopantoic acid or pantoic acid, and optionally salts thereof, can moreover be added to the culture medium to additionally increase the pantothenic acid production. The starting substances mentioned can be added to the culture in the form of a single batch, or can be fed in during the culture in a suitable manner.

Basic compounds, such as sodium hydroxide, potassium hydroxide, ammonia, or acid compounds, such as phosphoric acid or sulfuric acid, can be employed in a suitable manner to control the pH. Antifoams, such as, for example, fatty acid polyglycol esters, can be employed to control the development of foam. Suitable substances having a selective action, for example antibiotics, can be added to the medium to maintain the stability of plasmids. To maintain aerobic conditions, oxygen or oxygen-containing gas mixtures, such as, for example, air, are introduced into the culture. The temperature of the culture is usually 20° C. to 45° C., and preferably 25° C. to 40° C. Culturing is continued until a maximum of pantothenic acid has formed. This target is usually reached within 10 hours to 160 hours.

The concentration of pantothenic acid formed can be determined with known chemical (Velisek; Chromatographic Science 60, 515–560 (1992)) or microbiological methods, such as, for example, the *Lactobacillus plantarum* test (DIFCO MANUAL, $10^{th}$ Edition, p. 1100–1102; Michigan, USA).

The following microorganism has been deposited at the Deutsche Sammlung für Mikroorganismen und Zellkulturen (DSMZ=German Collection of Microorganisms and Cell Cultures, Braunschweig, Germany) in accordance with the Budapest Treaty:

*Corynebacterium glutamicum* DSM5715/pT-pfkAexp was deposited on Jan. 25, 2000 as DSM13253.

Having generally described this invention, a further understanding can be obtained by reference to certain specific examples which are provided herein for purposes of illustration only, and are not intended to be limiting unless otherwise specified.

EXAMPLES

For this purpose, experiments were carried out with the isoleucine-requiring strain ATCC13032ΔilvA and the plasmid pND-D2. The strain ATCC13032ΔilvA has been deposited as DSM12455 at the Deutsche Sammlung für Mikroorganismen und Zellkulturen [German Collection of Microorganisms and Cell Cultures] in Braunschweig (Germany) in accordance with the Budapest Treaty. The plasmid pND-D2 containing the panD gene is described in Dusch et al. (Applied and Environmental Microbiology 65(4), 1530–1539 (1999)) and is also deposited in the form of the strain *Corynebacterium glutamicum* ATCC13032/pND-D2 as DSM12438 at the Deutsche Sammlung fur Mikroorganismen und Zellkulturen [German Collection of Microorganisms and Cell Cultures] in Braunschweig (Germany) in accordance with the Budapest Treaty.

Example 1

Preparation of a Genomic Cosmid Gene Library from *Corynebacterium glutamicum* ATCC 13032

Chromosomal DNA from *Corynebacterium glutamicum* ATCC 13032 was isolated as described by Tauch et al. (1995, Plasmid 33:168–179) and partly cleaved with the restriction enzyme Sau3AI (Amersham Pharmacia, Freiburg, Germany, Product Description Sau3AI, Code no. 27-0913-02). The DNA fragments were dephosphorylated with shrimp alkaline phosphatase (Roche Molecular Biochemicals, Mannheim, Germany, Product Description SAP, Code no. 1758250). The DNA of the cosmid vector SuperCos1 (Wahl et al. (1987) Proceedings of the National Academy of Sciences USA 84:2160–2164), obtained from Stratagene (La Jolla, USA, Product Description SuperCos1 Cosmid Vector Kit, Code no. 251301) was cleaved with the restriction enzyme XbaI (Amersham Pharmacia, Freiburg, Germany, Product Description XbaI, Code no. 27-0948-02) and likewise dephosphorylated with shrimp alkaline phosphatase. The cosmid DNA was then cleaved with the restriction enzyme BamHI (Amersham Pharmacia, Freiburg, Germany, Product Description BamHI, Code no. 27-0868-04). The cosmid DNA treated in this manner was mixed with the treated ATCC 13032 DNA and the batch was treated with T4 DNA ligase (Amersham Pharmacia, Freiburg, Germany, Product Description T4-DNA-Ligase, Code no.27-0870-04). The ligation mixture was then packed in phages with the aid of Gigapack II XL Packing Extract (Stratagene, La Jolla, USA, Product Description Gigapack II XL Packing Extract, Code no. 200217). For infection of the *E. coli* strain NM554 (Raleigh et al. 1988, Nucleic Acid Research 16:1563–1575)

the cells were taken up in 10 mM MgSO$_4$ and mixed with an aliquot of the phage suspension. The infection and titering of the cosmid library were carried out as described by Sambrook et al. (1989, Molecular Cloning: A laboratory Manual, Cold Spring Harbor), the cells being plated out on LB agar (Lennox, 1955, Virology, 1:190) with 100 µg/ml ampicillin. After incubation overnight at 37° C., recombinant individual clones were selected.

Example 2
Isolation and Sequencing of the pfkA Gene

The cosmid DNA of an individual colony was isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02). The DNA fragments were dephosphorylated with shrimp alkaline phosphatase (Roche Molecular Biochemicals, Mannheim, Germany, Product Description SAP, Product No. 1758250). After separation by gel electrophoresis, the cosmid fragments in the size range of 1500 to 2000 bp were isolated with the QiaExII Gel Extraction Kit (Product No. 20021, Qiagen, Hilden, Germany). The DNA of the sequencing vector pZero-1, obtained from Invitrogen (Groningen, The Netherlands, Product Description Zero Background Cloning Kit, Product No. K2500-01) was cleaved with the restriction enzyme BamHI (Amersham Pharmacia, Freiburg, Germany, Product Description BamHI, Product No. 27-0868-04). The ligation of the cosmid fragments in the sequencing vector pZero-1 was carried out as described by Sambrook et al. (1989, Molecular Cloning: A laboratory Manual, Cold Spring Harbor), the DNA mixture being incubated overnight with T4 ligase (Pharmacia Biotech, Freiburg, Germany). This ligation mixture was then electroporated (Tauch et al. 1994, FEMS Microbiol Letters, 123:343–7) into the *E. coli* strain DH5αMCR (Grant, 1990, Proceedings of the National Academy of Sciences U.S.A., 87:4645–4649) and plated out on LB agar (Lennox, 1955, Virology, 1:190) with 50 µg/ml zeocin. The plasmid preparation of the recombinant clones was carried out with Biorobot 9600 (Product No. 900200, Qiagen, Hilden, Germany). The sequencing was carried out by the dideoxy chain termination method of Sanger et al. (1977, Proceedings of the National Academy of Sciences U.S.A., 74:5463–5467) with modifications according to Zimmermann et al. (1990, Nucleic Acids Research, 18:1067). The "RR dRhodamin Terminator Cycle Sequencing Kit" from PE Applied Biosystems (Product No. 403044, Weiterstadt, Germany) was used. The separation by gel electrophoresis and analysis of the sequencing reaction were carried out in a "Rotiphoresis NF Acrylamide/Bisacrylamide" Gel (29:1) (Product No. A124.1, Roth, Karlsruhe, Germany) with the "ABI Prism 377" sequencer from PE Applied Biosystems (Weiterstadt, Germany).

The raw sequence data obtained were then processed using the Staden program package (1986, Nucleic Acids Research, 14:217–231) version 97-0. The individual sequences of the pZerol derivatives were assembled to a continuous contig. The computer-assisted coding region analysis was prepared with the XNIP program (Staden, 1986, Nucleic Acids Research, 14:217–231). Further analyses were carried out with the "BLAST search program" (Altschul et al., 1997, Nucleic Acids Research, 25:3389–3402), against the non-redundant databank of the "National Center for Biotechnology Information" (NCBI, Bethesda, Md., USA).

The nucleotide sequence obtained is shown in SEQ ID NO 1. Analysis of the nucleotide sequence showed an open reading frame of 1029 base pairs, which was called the pfkA gene. The pfkA gene codes for a protein of 343 amino acids, which is shown in SEQ ID NO 2.

Example 3
Preparation of a Plasmid for Expression of pfkA in *Corynebacterium glutamicum*

3.1. Cloning of pfkA in the Vector pCR-Blunt2

Chromosomal DNA from *Corynebacterium glutamicum* ATCC 13032 became as by [sic] Tauch et al. (1995, Plasmid 33:168–179). On the basis of the sequence of the pfkA gene known for *C. glutamicum* from example 2, the following oligonucleotides were chosen for the polymerase chain reaction:

pfkA-exp

5'-AAC TGC AGC TCT GGC GAT TA-3'   (SEQ ID NO:3)

pfk-ex2

5'-AAC TAT CCA AAC ATT GCC TG-3'   (SEQ ID NO:4)

The primers shown were synthesized by MWG Biotech (Ebersberg, Germany) and the PCR reaction was carried out by the standard PCR method of Innis et al. (PCR protocols. A guide to methods and applications, 1990, Academic Press) with Pwo-Polymerase from Roche Diagnostics GmbH (Mannheim, Germany). With the aid of the polymerase chain reaction, a DNA fragment approx. 1160 bp in size was isolated, this carrying the pfkA gene.

The amplified DNA fragment was ligated with the Zero Blunt TOPO PCR Cloning Kit from Invitrogen Corporation (Carlsbad, Calif., USA; Catalogue Number K2800-20) in the vector pCR-Blunt II-TOPO vector (Shuman at al., (1994) Journal of Biological Chemistry. 269:32678–32684; Bernard et al., (1983) Journal of Molecular Biology. 234:534–541). The *E. coli* strain Top10 (Grant et al. (1990) Proceedings of the National Academy of Sciences, USA. 87:4645–4649) was then transformed with the ligation batch. Selection for plasmid-carrying cells was made by plating out the transformation batch on LB agar (Sambrook et al., Molecular cloning: a laboratory manual. 2$^{nd}$ Ed. Cold Spring Harbor Laboratory Press, Cold Spring Harbor, N.Y.), which had been supplemented with 50 mg/l kanamycin. Plasmid DNA was isolated from a transformant with the aid of the QIAprep Spin Miniprep Kit from Qiagen and checked by restriction with the restriction enzyme EcoRI and subsequent agarose gel electrophoresis (0.8%). The plasmid was called pCRB1-pfkAexp1.

3.2. Preparation of the Shuttle Vector pEC-T18mob2

Figure 2:
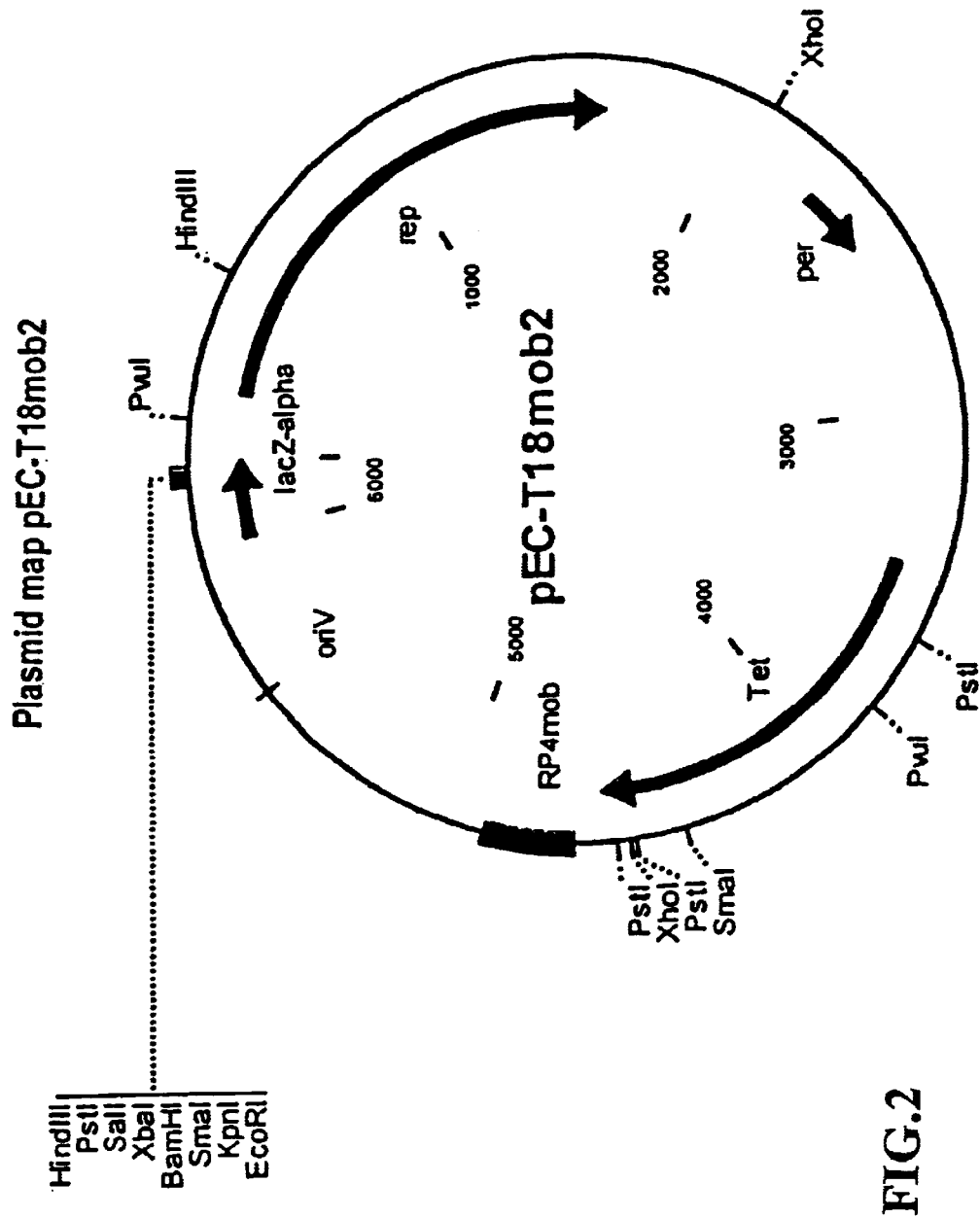
FIG. 2: Plasmid map of pEC-T18mob2

The *E. coli-C. glutamicum* shuttle vector was constructed according to the prior art. The vector contains the replication region rep of the plasmid pGA1 including the replication effector per (U.S. Pat. No. 5,175,108; Nesvera et al., Journal of Bacteriology 179, 1525–1532 (1997)), the tetracycline resistance-imparting tetA(Z) gene of the plasmid pAG1 (U.S. Pat. No. 5,158,891; gene library entry at the National Center for Biotechnology Information (NCBI, Bethesda, Md., USA) with accession number AF121000), the replication region oriV of the plasmid pMB1 (Sutcliffe, Cold Spring Harbor Symposium on Quantitative Biology 43, 77–90 (1979)), the lacZα gene fragment including the lac promoter and a multiple cloning site (mcs) (Norrander et al. Gene 26, 101–106 (1983)) and the mob region of the plasmid RP4 (Simon et al.,(1983) Bio/Technology 1:784–791). The vector constructed was transformed in the *E. coli* strain DH5α (Hanahan, In: DNA cloning. A practical approach. Vol. I. IRL-Press, Oxford, Washington D.C., USA). Selection for plasmid-carrying cells was made by plating out the transformation batch on LB agar (Sambrook et al., Molecular cloning: a laboratory manual. $2^{nd}$ Ed. Cold Spring Harbor Laboratory Press, Cold Spring Harbor, N.Y.), which had been supplemented with 5 mg/l tetracycline. Plasmid DNA was isolated from a transformant with the aid of the QIAprep Spin Miniprep Kit from Qiagen and checked by restriction with the restriction enzyme EcoRI and HindIII [sic] subsequent agarose gel electrophoresis (0.8%). The plasmid was called pEC-T18mob2 and is shown in FIG. 2.

3.3. Cloning of pfkA in the Shuttle Vector pEC-T18mob2

The *E. coli-C. glutamicum* shuttle vector pEC-T18mob2 described in example 3.2 was used as the vector. DNA of this plasmid was cleaved completely with the restriction enzyme EcoRI and then dephosphorylated with shrimp alkaline phosphatase (Roche Molecular Biochemicals, Mannheim, Germany, Product Description SAP, Product No. 1758250).

The pfkA gene was isolated from the plasmid pCRB1-pfkAexp1 described in example 3.1. by complete cleavage with the enzyme EcoRI. The pfkA fragment approx. 1160 bp in size was isolated from the agarose gel with the QiaExII Gel Extraction Kit (Product No. 20021, Qiagen, Hilden, Germany).

The pfkA fragment obtained in this manner was mixed with the prepared vector pEC-T18mob2 and the batch was treated with T4 DNA ligase (Amersham Pharmacia, Freiburg, Germany, Product Description T4-DNA-Ligase, Code no.27-0870-04). The ligation batch was transformed in the *E. coli* strain DH5amcr (Grant et al., (1990). Proceedings of the National Academy of Sciences USA. 87: 4645–4649). Selection of plasmid-carrying cells was made by plating out the transformation batch on LB agar (Lennox, 1955, Virology, 1:190) with 5 mg/l tetracycline. After incubation overnight at 37° C., recombinant individual clones were selected. Plasmid DNA was isolated from a transformant with the Qiaprep Spin Miniprep Kit (Product No. 27106, Qiagen, Hilden, Germany) in accordance with the manufacturer's instructions and cleaved with the restriction enzyme EcoRI to check the plasmid by subsequent agarose gel electrophoresis. The resulting plasmid was called pT-pfkAexp. It is shown in FIG. 1.

Example 4
Preparation of the Strain ATCC13032ΔilvA/pND-D2, pT-pfkAexp

After electroporation (Tauch et.al., 1994, FEMS Microbiological Letters, 123:343–347) of the plasmid pND-D2 in the *C. glutamicum* strain ATCC13032ΔilvA and subsequent selection on LB agar (Lennox, 1955, Virology, 1:190–206), which had been supplemented with 25 μg/ml kanamycin, the strain ATCC13032ΔilvA/pND-D2 was obtained.

After electroporation of the plasmid pT-pfkAexp (example 3) in the *C. glutamicum* strain ATCC13032ΔilvA/pND-D2 and subsequent selection on LB agar, which had been supplemented with 25 μg/ml kanamycin and 10 μg/ml tetracycline, the strain ATCC13032ΔilvA/pND-D2, pT-pfkAexp was obtained.

Example 5
Preparation of Pantothenic Acid

The formation of pantothenate by the *C. glutamicum* strains ATCC13032ΔilvA/pND-D2 and ATCC13032ΔilvA/pND-D2, pT-pfkAexp was tested in medium CGXII (Keilhauer et al., 1993, Journal of Bacteriology, 175:5595–5603; table 1), which had been supplemented with 25 μg/ml kanamycin, 2 mM isoleucine and in the case of the strain ATCC13032ΔilvA/pND-D2, pT-pfkAexp with additionally 10 μg/ml tetracycline.

This medium is called *C. glutamicum* test medium in the following. In each case 50 ml of freshly prepared *C. glutamicum* test medium were inoculated with a 16 hours old preculture of the same medium such that the optical density of the culture suspension ($OD_{580}$) at the start of incubation was 0.1. The cultures were incubated at 30° C. and 130 rpm. After incubation for 5 hours, IPTG (isopropyl β-D-thiogalactoside was added in a final concentration of 1 mM. After incubation for 48 hours the optical density ($OD_{580}$) of the culture was determined and the cells were then removed by centrifugation at 5000 g for 10 minutes and the supernatant subjected to sterile filtration.

A Novaspec II photometer from Pharmacia (Freiburg, Germany) was employed at a measurement wavelength of 580 nm for determination of the optical density.

The D-pantothenate in the culture supernatant was quantified by means of Lactobacillus plantarum ATCC 8014 in accordance with the instructions in the handbook of DIFCO (DIFCO MANUAL, $10^{th}$ Edition, p. 1100–1102; Michigan, USA).

The hemi-calcium salt of pantothenate from Sigma (Deisenhofen, Germany) was used for the calibration.

The result is shown in table 2.

TABLE 1

| Substance | Amount per liter | Comments |
|---|---|---|
| $(NH_4)_2 SO_2$ | 20 g | |
| Urea | 5 g | |
| $KH_2PO_4$ | 1 g | |
| $K_2HPO_4$ | 1 g | |
| $MgSO_4 * 7 H_2O$ | 0.25 g | |
| MOPS | 42 g | |
| $CaCl_2$ | 10 mg | |
| $FeSO_4 * 7 H_2O$ | 10 mg | |
| $MnSO_4 * H_2O$ | 10 mg | |
| $ZnSO_4 * 7 H_2O$ | 1 mg | |
| $CuSO_4$ | 0.2 mg | |
| $NiCl_2 * 6 H_2O$ | 0.02 mg | |
| Biotin | 0.5 mg | |
| Glucose | 40 g | autoclave separately |
| Protocatechuic acid | 0.03 mg | sterile filtration |

TABLE 2

| Strain | Cell density $OD_{580}$ | Concentration (ng/ml) |
|---|---|---|
| ATCC13032ΔilvA/pND-D2 | 11.5 | 47.9 |
| ATCC13032ΔilvA/pND-D2, pT-pfkAexp | 12.8 | 119.9 |

The abbreviations and designations used have the following meaning.

| | |
|---|---|
| Tet: | Resistance gene for tetracycline |
| oriV: | Plasmid-coded replication origin of *E. coli* |
| RP4mob: | mob region for mobilizing the plasmid |
| rep: | Plasmid-coded replication origin from *C. glutamicum* plasmid pGA1 |
| per: | Gene for controlling the number of copies from pGA1 |
| lacZ-alpha: | lacZα gene fragment (N-terminus) of the β-galactosidase gene |
| 'lacZa': | 3' end of the lacZα gene fragment |
| lacZ-alpha': | 5' end of the lacZα gene fragment |
| pfkA: | pfkA gene from *C. glutamicum* ATCC13032 |

| | |
|---|---|
| BamHI: | Cleavage site of the restriction enzyme BamHI |
| EcoRI: | Cleavage site of the restriction enzyme EcoRI |
| HindIII: | Cleavage site of the restriction enzyme HindIII |
| KpnI: | Cleavage site of the restriction enzyme KpnI |
| PstI: | Cleavage site of the restriction enzyme PstI |
| PvuI: | Cleavage site of the restriction enzyme PvuI |
| SalI: | Cleavage site of the restriction enzyme SalI |
| SacI: | Cleavage site of the restriction enzyme SacI |
| SmaI: | Cleavage site of the restriction enzyme SmaI |
| SphI: | Cleavage site of the restriction enzyme SphI |
| XbaI: | Cleavage site of the restriction enzyme XbaI |
| XhoI: | Cleavage site of the restriction enzyme XhoI |

Obviously, numerous modifications and variations on the present invention are possible in light of the above teachings. It is therefore to be understood that within the scope of the appended claims, the invention may be practiced otherwise than as specifically described herein.

What is claimed is:

1. A process for preparing D-pantothenic acid comprising a. culturing a Coryneform bacteria comprising an overexpressed pfkA gene in a medium suitable for expression of the pfkA gene; wherein said pfkA gene comprises the nucleotide sequence of SEQ ID NO:1; or a nucleotide sequence which hybridizes under stringent conditions to the complement of SEQ ID NO:1 and encodes a polypeptide having phosphofructokinase activity, wherein said stringent conditions comprise washing in 5×SSC at a temperature from 50 to 68° C.; and b. collecting the D-pantothenic acid produced.

2. The process of claim 1, wherein said pfKA gene encodes a polypeptide comprising the amino acid sequence of SEQ ID NO:2.

3. The process of claim 1, wherein said Coryneform bacteria is *Corynebacterium glutamicum*.

4. The process of claim 1, wherein said Coryneform bacterium is selected from the group consisting of *Coryneformbacterium acteoglutamicum, Coryneformbacterium acetoacidophilum, Coryneformbacterium thermoaminogenes, Brevibacterium flavum, Brevibacterium lactofermentum,* and *Brevibacterium divaricatum*.

5. The process of claim 1, wherein said Coryneform bacterium is *Corynebacterium glutamicum* DSM13253.

6. *Corynebacterium glutamicum* DSM13253.

7. A process for producing D-pantothnic acid comprising:

a. transforming a Coryneform bacteria with a vector comprising a pfkA gene, wherein said pfkA gene is under the control of a promoter which allows the over-expression of said pfkA gene, wherein said pfkA gene comprises the nucleotide sequence of SEQ ID NO:1; or wherein said pfkA gene comprises a nucleotide sequence which hybridizes under stringent conditions to the complement of SEQ ID NO:1 and encodes a polypeptide having phosphofructokinase activity, wherein said stringent conditions comprise washing in 5×SSC at a temperature from 50 to 68° C.;

b. culturing said transformed Coryneform bacteria in a medium suitable for expression of the pfkA gene; and c. collecting the D-pantothenic acid produced.

8. The process of claim 7, wherein said pfKA gene encodes a polypeptide comprising the amino acid sequence of SEQ ID NO:2.

9. The process of claim 7, wherein said Coryneform bacteria is *Corynebacterium glutamicum*.

10. The process of claim 7, wherein said Coryneform bacterium is selected from the group consisting of *Corynebacterium acteoglutamicum, Corynebacterium acetoacidophilum, Corynebacterium thermoaminogenes, Brevibacterium flavum, Brevibacterium lactofermentum,* and *Brevibacterium divaricatum*.

11. The process of claim 7, wherein said Coryneform bacterium is *Corynebacterium glutamicum* DSM13253.

12. Coryneform bacteria comprising an overexpressed pfkA gene, wherein said pfkA gene comprises the nucleotide sequence of SEQ ID NO:1; or wherein said pfkA gene comprises a nucleotide sequence which hybridizes under stringent conditions to the complement of SEQ ID NO:1 and encodes a polypeptide having phosphofructokinase activity, wherein said stringent conditions comprise washing in 5×SSC at a temperature from 50 to 68° C.

13. The Coryneform bacteria of claim 12, wherein said phosphofructokinase polypeptide comprises the amino acid sequence of SEQ ID NO:2.

14. The method of claim 1, wherein said pfkA gene comprises SEQ ID NO:1.

15. The method of claim 7, wherein said pfkA gene comprises SEQ ID NO:1.

16. The Coryneform bacteria of claim 12, wherein said pfkA gene comprises SEQ ID NO:1.

* * * * *

SEQUENCE LISTING

```
<160> NUMBER OF SEQ ID NOS: 4

<210> SEQ ID NO 1
<211> LENGTH: 1274
<212> TYPE: DNA
<213> ORGANISM: Corynebacterium glutamicum
<220> FEATURE:
<221> NAME/KEY: CDS
<222> LOCATION: (143)..(1171)

<400> SEQUENCE: 1
gtcgatttgt taatgaaact gcagctctgg cgattaaata agatggtcag agacagtttt      60
ttggcctgtc aacccctgtg attctcttat ttttgggtga ttgttccggc gcgggtgttg     120
tgatgggttt aatatggaag ac atg cga att gct act ctc acg tca ggc ggc     172
                         Met Arg Ile Ala Thr Leu Thr Ser Gly Gly
                           1               5                  10 gac tgc ccc gga cta aac gcc gtc atc cga gga atc gtc cgc aca gcc     220
Asp Cys Pro Gly Leu Asn Ala Val Ile Arg Gly Ile Val Arg Thr Ala
                 15                  20                  25 agc aat gaa ttt ggc tcc acc gtc gtt ggt tat caa gac ggt tgg gaa     268
Ser Asn Glu Phe Gly Ser Thr Val Val Gly Tyr Gln Asp Gly Trp Glu
         30                  35                  40 gga ctg tta ggc gat cgt cgc gta cag ctg tat gac gat gaa gat att     316
Gly Leu Leu Gly Asp Arg Arg Val Gln Leu Tyr Asp Asp Glu Asp Ile
     45                  50                  55 gac cga atc ctc ctt cga ggc ggc acc att ttg ggc act ggt cgc ctc     364
Asp Arg Ile Leu Leu Arg Gly Gly Thr Ile Leu Gly Thr Gly Arg Leu
 60                  65                  70 cat ccg gac aag ttt aag gcc gga att gat cag att aag gcc aac tta     412
His Pro Asp Lys Phe Lys Ala Gly Ile Asp Gln Ile Lys Ala Asn Leu
 75                  80                  85                  90 gaa gac gcc ggc atc gat gcc ctt atc cca atc ggt ggc gaa gga acc     460
Glu Asp Ala Gly Ile Asp Ala Leu Ile Pro Ile Gly Gly Glu Gly Thr
                 95                 100                 105 ctg aag ggt gcc aag tgg ctg tct gat aac ggt atc cct gtt gtc ggt     508
Leu Lys Gly Ala Lys Trp Leu Ser Asp Asn Gly Ile Pro Val Val Gly
        110                 115                 120 gtc cca aag acc att gac aat gac gtg aat ggc act gac ttc acc ttc     556
Val Pro Lys Thr Ile Asp Asn Asp Val Asn Gly Thr Asp Phe Thr Phe
    125                 130                 135 ggt ttc gat act gct gtg gca gtg gct acc gac gct gtt gac cgc ctg     604
Gly Phe Asp Thr Ala Val Ala Val Ala Thr Asp Ala Val Asp Arg Leu
140                 145                 150 cac acc acc gct gaa tct cac aac cgt gtg atg atc gtg gag gtc atg     652
His Thr Thr Ala Glu Ser His Asn Arg Val Met Ile Val Glu Val Met
155                 160                 165                 170
```

```
ggc cgc cac gtg ggt tgg att gct ctg cac gca ggt atg gcc ggc ggt      700
Gly Arg His Val Gly Trp Ile Ala Leu His Ala Gly Met Ala Gly Gly
            175                 180                 185 gct cac tac acc gtt att cca gaa gta cct ttc gat att gca gag atc      748
Ala His Tyr Thr Val Ile Pro Glu Val Pro Phe Asp Ile Ala Glu Ile
            190                 195                 200 tgc aag gcg atg gaa cgt cgc ttc cag atg ggc gag aag tac ggc att      796
Cys Lys Ala Met Glu Arg Arg Phe Gln Met Gly Glu Lys Tyr Gly Ile
            205                 210                 215 atc gtc gtt gcg gaa ggt gcg ttg cca cgc gaa ggc acc atg gag ctt      844
Ile Val Val Ala Glu Gly Ala Leu Pro Arg Glu Gly Thr Met Glu Leu
            220                 225                 230 cgt gaa ggc cac att gac cag ttc ggt cac aag acc ttc acg gga att      892
Arg Glu Gly His Ile Asp Gln Phe Gly His Lys Thr Phe Thr Gly Ile
235                 240                 245                 250 gga cag cag atc gct gat gag atc cac gtg cgc ctc ggc cac gat gtt      940
Gly Gln Gln Ile Ala Asp Glu Ile His Val Arg Leu Gly His Asp Val
                255                 260                 265 cgt acg acc gtt ctt ggc cac att caa cgt ggt gga acc cca act gct      988
Arg Thr Thr Val Leu Gly His Ile Gln Arg Gly Gly Thr Pro Thr Ala
            270                 275                 280 ttc gac cgt gtt ctg gcc act cgt tat ggt gtt cgt gca gct cgt gcg     1036
Phe Asp Arg Val Leu Ala Thr Arg Tyr Gly Val Arg Ala Ala Arg Ala
            285                 290                 295 tgc cat gag gga agc ttt gac aag gtt gtt gct ttg aag ggt gag agc     1084
Cys His Glu Gly Ser Phe Asp Lys Val Val Ala Leu Lys Gly Glu Ser
            300                 305                 310 att gag atg atc acc ttt gaa gaa gca gtc gga acc ttg aag gaa gtt     1132
Ile Glu Met Ile Thr Phe Glu Glu Ala Val Gly Thr Leu Lys Glu Val
315                 320                 325                 330 cca ttc gaa cgc tgg gtt act gcc cag gca atg ttt gga tagttttcg       1181
Pro Phe Glu Arg Trp Val Thr Ala Gln Ala Met Phe Gly
                335                 340 ggcttttatc aacagccaat aacagctctt tcgcccattg aggtggaggg gctgtttttt   1241
catgccgtaa ggaaagtgca agtaagtgaa atc                                1274

<210> SEQ ID NO 2
<211> LENGTH: 343
<212> TYPE: PRT
<213> ORGANISM: Corynebacterium glutamicum

<400> SEQUENCE: 2

Met Arg Ile Ala Thr Leu Thr Ser Gly Gly Asp Cys Pro Gly Leu Asn
1               5                   10                  15

Ala Val Ile Arg Gly Ile Val Arg Thr Ala Ser Asn Glu Phe Gly Ser
                20                  25                  30

Thr Val Val Gly Tyr Gln Asp Gly Trp Glu Gly Leu Leu Gly Asp Arg
            35                  40                  45

Arg Val Gln Leu Tyr Asp Asp Glu Asp Ile Asp Arg Ile Leu Leu Arg
        50                  55                  60

Gly Gly Thr Ile Leu Gly Thr Gly Arg Leu His Pro Asp Lys Phe Lys
65                  70                  75                  80

Ala Gly Ile Asp Gln Ile Lys Ala Asn Leu Glu Asp Ala Gly Ile Asp
                85                  90                  95

Ala Leu Ile Pro Ile Gly Gly Glu Gly Thr Leu Lys Gly Ala Lys Trp
            100                 105                 110

Leu Ser Asp Asn Gly Ile Pro Val Val Gly Val Pro Lys Thr Ile Asp
        115                 120                 125
```

```
Asn Asp Val Asn Gly Thr Asp Phe Thr Phe Gly Phe Asp Thr Ala Val
        130                 135                 140

Ala Val Ala Thr Asp Ala Val Asp Arg Leu His Thr Thr Ala Glu Ser
145                 150                 155                 160

His Asn Arg Val Met Ile Val Glu Val Met Gly Arg His Val Gly Trp
                165                 170                 175

Ile Ala Leu His Ala Gly Met Ala Gly Gly Ala His Tyr Thr Val Ile
                180                 185                 190

Pro Glu Val Pro Phe Asp Ile Ala Glu Ile Cys Lys Ala Met Glu Arg
            195                 200                 205

Arg Phe Gln Met Gly Glu Lys Tyr Gly Ile Ile Val Val Ala Glu Gly
        210                 215                 220

Ala Leu Pro Arg Glu Gly Thr Met Glu Leu Arg Glu Gly His Ile Asp
225                 230                 235                 240

Gln Phe Gly His Lys Thr Phe Thr Gly Ile Gly Gln Gln Ile Ala Asp
                245                 250                 255

Glu Ile His Val Arg Leu Gly His Asp Val Arg Thr Thr Val Leu Gly
                260                 265                 270

His Ile Gln Arg Gly Gly Thr Pro Thr Ala Phe Asp Arg Val Leu Ala
            275                 280                 285

Thr Arg Tyr Gly Val Arg Ala Ala Arg Ala Cys His Glu Gly Ser Phe
290                 295                 300

Asp Lys Val Val Ala Leu Lys Gly Glu Ser Ile Glu Met Ile Thr Phe
305                 310                 315                 320

Glu Glu Ala Val Gly Thr Leu Lys Glu Val Pro Phe Glu Arg Trp Val
                325                 330                 335

Thr Ala Gln Ala Met Phe Gly
            340

<210> SEQ ID NO 3
<211> LENGTH: 20
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 3
aactgcagct ctggcgatta                                              20

<210> SEQ ID NO 4
<211> LENGTH: 20
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 4
aactatccaa acattgcctg                                              20
```